United States Patent [19]

Jenkins, III et al.

[11] 4,371,977

[45] Feb. 1, 1983

[54] METHOD FOR DETECTING SOLIDIFICATION IN A MIXED PHASE CONTAINER

[75] Inventors: John M. Jenkins, III, South Charleston, W. Va.; Max E. Carter, Sr., Victoria, Tex.; Michael L. Green, Scott Depot, W. Va.; Marvin E. Cavender, Victoria, Tex.

[73] Assignee: Union Carbide Corporation, Danbury, Conn.

[21] Appl. No.: 160,288

[22] Filed: Jun. 17, 1980

[51] Int. Cl.³ .......................................... G01N 23/00
[52] U.S. Cl. ........................................ 378/51; 378/54; 526/59
[58] Field of Search ................... 250/358 R, 359, 357, 250/432 R; 356/436, 442, 39; 526/59, 348, 348.2–348.7

[56] References Cited

U.S. PATENT DOCUMENTS 2,725,782 12/1955 Worley ................................. 356/39
2,922,884 1/1960 Fearnside ........................ 250/358 R
3,255,346 6/1966 Brunton et al. ..................... 250/357
4,038,550 7/1977 Wassen et al. ...................... 250/360
4,282,433 8/1981 Löffel ................................. 250/359

OTHER PUBLICATIONS

News Release #7639, "Ohmart Introduces Versatile New Levelart Multi/1500 Multipoint Level Measurement System", Nov. 27, 1979.

Ohmart Interoffice Correspondence, "Introduction of New Product, Level Art Multi/1500 Series, Multipoint Level Measurement System", November BB, 1979.

Primary Examiner—Alfred E. Smith
Assistant Examiner—Carolyn E. Fields
Attorney, Agent, or Firm—Clement J. Vicari

[57] ABSTRACT

A method for detecting solidification in a mixed phase low pressure fluidized bed olefin polymerization reactor having volume comprising:

A. disposing a radiation source and a radiation detector such that radiation from said radiation source will pass through a radiation path through at least a portion of the volume of said container to reach said radiation detector, B. detecting solidification in said radiation path by noting a decrease in the amount of radiation reaching said radiation detector.

4 Claims, 5 Drawing Figures

METHOD FOR DETECTING SOLIDIFICATION IN A MIXED PHASE CONTAINER

BACKGROUND

This invention relates, in general, to mixed phase containers such as fluidized bed reactors or slurry tanks. More specifically, this invention concerns a method for detecting solidification or chunks in mixed phase containers.

One prior art method of detecting solidification in mixed phase containers is to use sight glasses. However, sight glasses tend to become coated with material rendering them non-transparent very shortly after they are placed in use.

A radiation source and detector has been used to detect the level of solids in various devices such as storage bins. However, use of such devices has been limited to relatively thin-walled containers having no mixed phase. Hence there exists a need to detect relatively small chunks of solidification disposed within a mixed container.

OBJECTS

Accordingly, it is an object of this invention to provide a reliable method of detecting solidification within a mixed phase container.

SUMMARY

This and other objects are accomplished by the present invention, one aspect of which comprises a method for detecting solidification in a mixed phase container having volume comprising:

A. disposing a radiation source and a radiation detector such that radiation from said radiation source will pass through a radiation path through at least a portion of the volume of said container to reach said radiation detector, B. detecting solidification in said radiation path by noting a decrease in the amount of radiation reaching said radiation detector.

A second aspect of the invention comprises apparatus for containing a mixed phase comprising:

A. a mixed phase container, having volume,
B. a radiation source, and
C. a radiation detector, said source and detector disposed such that a radiation path between said source and said detector passes through at least a portion of the volume of said container. Preferably the container will be symmetrical and the radiation source will be placed on a center line of the container with a plurality of radiation detectors disposed at different locations outside the reactor, thereby creating an equal plurality of radiation paths between the radiation source and the radiation detectors.

The term "mixed phase container" as used throughout the present specification and claims is intended to mean a container for holding at least two phases, at least one of which is solid, wherein the phases are intermingled with each other. A typical mixed phase container would be a fluidized-bed, low pressure olefin polymerization reactor wherein olefins are polymerized at pressures below about 300 psig. However, any container holding more than one phase, one of which is solid, will find use for this invention. Other mixed phase containers include slurry tanks and some dryers and coolers.

DETAILED DESCRIPTION OF THE INVENTION

Figure 1:
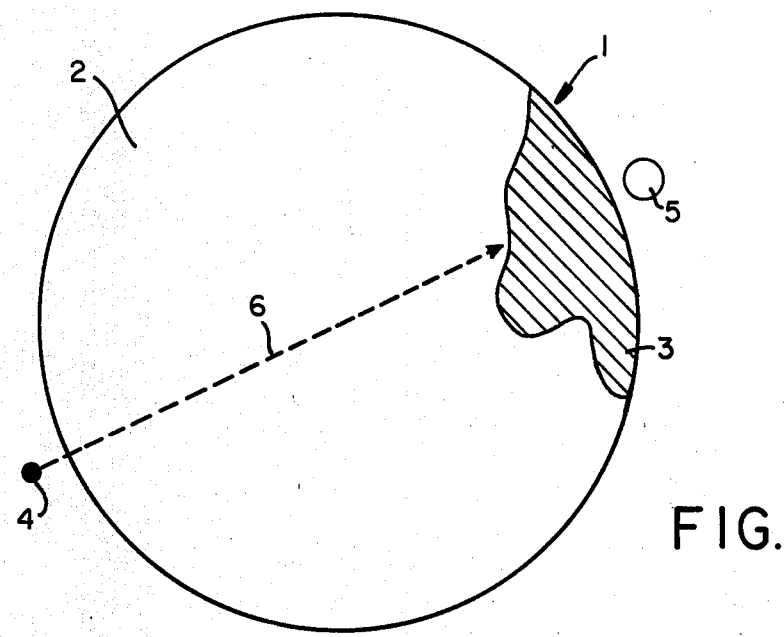
FIG. 1 illustrates a cut away plan view of a mixed phase container employing one embodiment of the invention.

FIG. 1 illustrates a cut away plan view of a mixed phase container 1 having volume 2 in which a mixed phase, such as a fluidized-bed, is contained. Radiation source 4 and radiation detector 5 are disposed such that radiation will pass through radiation path 6 which passes through volume 2 of the container to reach radiation detector 5. If a chunk of solid material 3 forms, the amount of radiation reaching detector 5 will be decreased, thereby indicating the presence of chunk 3. Surprisingly, a relatively small chunk has been found to cause a detectable decrease in the quantity of radiation reaching the radiation detector, despite the fact that the radiation must pass through relatively thick walls and through the relatively dense mixed phases.

Figure 2:
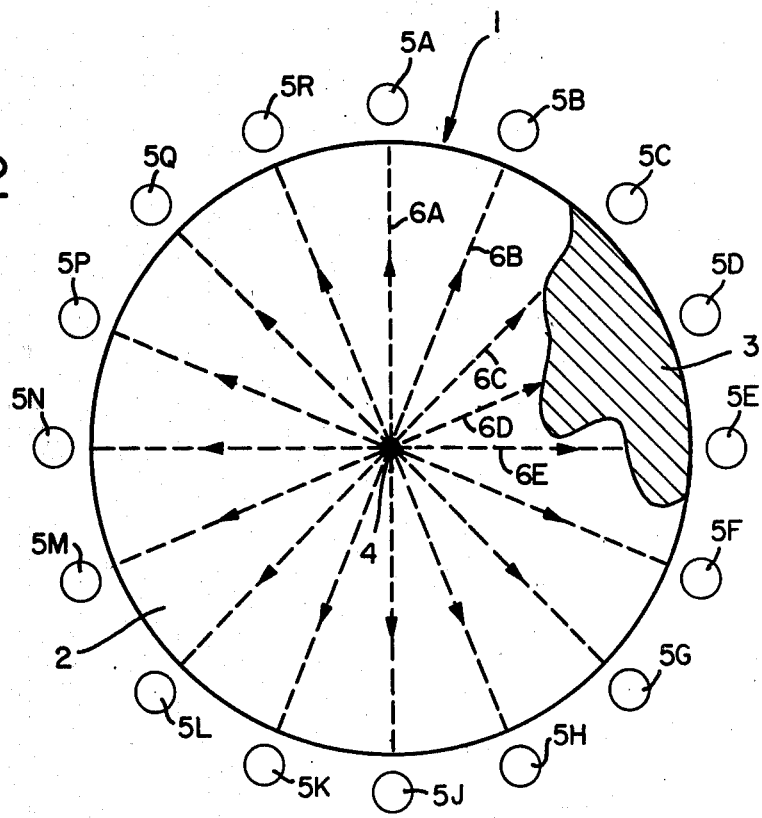
FIG. 2 illustrates a cut away plan view of a mixed phase container employing a more preferred embodiment of the invention.

FIG. 2 illustrates a more preferred embodiment of the invention. Here mixed phase container 1 has radiation source 4 disposed within the container. Preferably the mixed phase container is symmetrical about a center line and radiation source 4 is placed on the center line as shown in FIG. 2. Disposed outside the container are 16 radiation detectors, 5A through 5R. Radiation from source 4 passes through paths 6A, 6B, 6C etc. to reach the radiation detectors. If chunk 3 forms inside the container, it is likely to fall within one or more of the radiation paths thereby causing a decrease in the amount of radiation reaching one or more of the radiation detectors. In FIG. 2 chunk 3 has formed within paths 6C, 6D and 6E, which would cause a decrease in the radiation detected by detectors 5C, 5D and 5E.

In designing systems to using the invention, previous experience with individual mixed phase containers will show where chunks are most likely to form. It is then desirable to dispose the radiation source and detectors such that the radiation paths pass through places where chunk formation is expected.

It is preferred that the invention be applied as a highly automated system wherein electronic equipment, well known to those skilled in the art, is used to continuously monitor the amount of radiation detected by the radiation detectors. If a low level of radiation is detected, indicating solidification within the container, then it is preferred that the electronic equipment activate an alarm.

Figure 3:
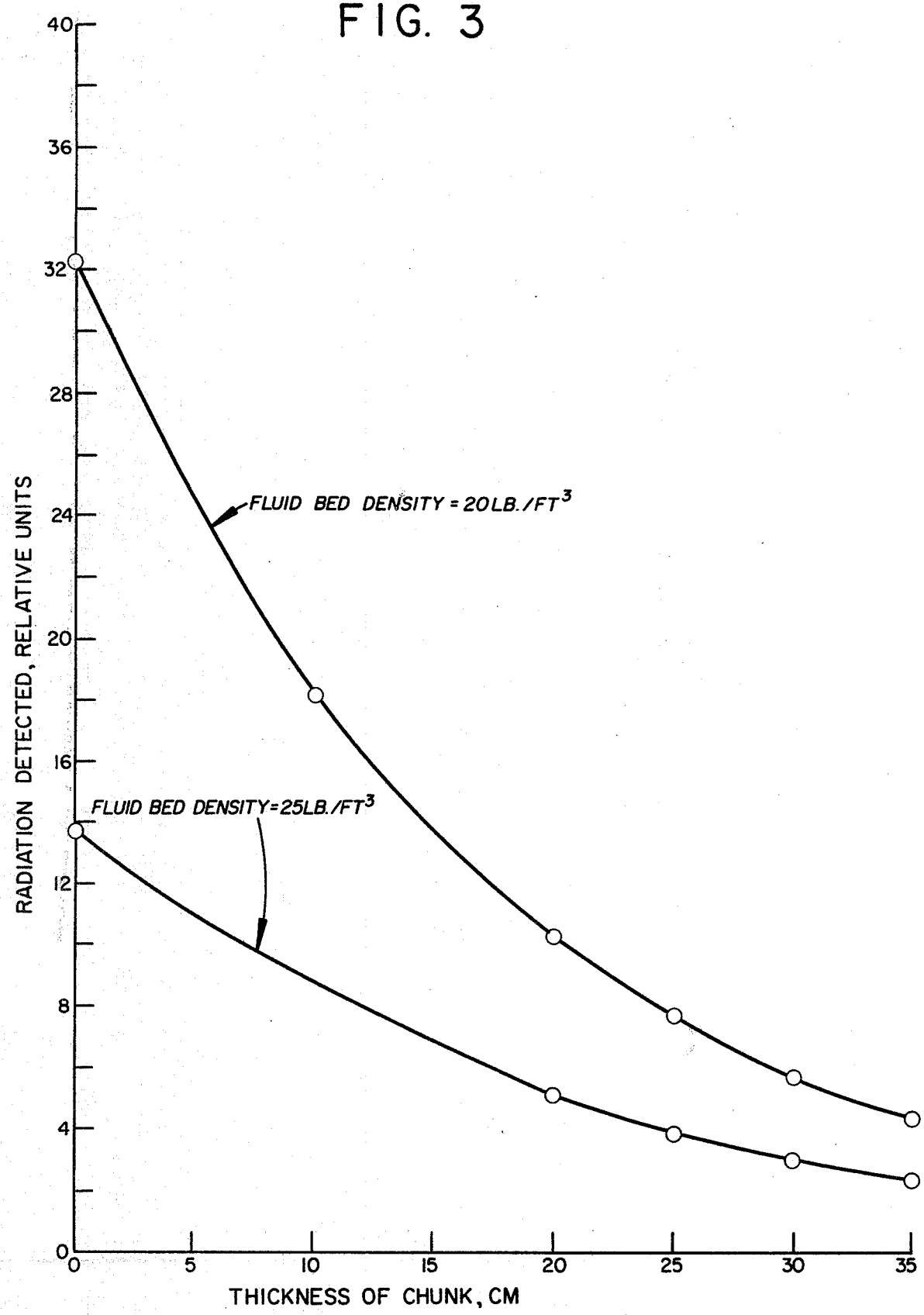
FIG. 3 is a theoretical graph used for estimating the effect of varying mixed phase density on the detectability of chunks in the container.

FIG. 3 is a theoretical graph used for estimating the effect of varying mixed phase density on the detectability of chunks in the container. In FIG. 3 the amount of radiation calculated to be detected by a radiation detector is plotted on the vertical axis, while the chunk thickness in centimeters is plotted on the horizontal axis. Conventional calculation techniques, well known to those skilled in the art may be used. As illustrated by the example below, the calculation need not be extremely accurate. The lower curve assumes a mixed phase density of 25 pounds per cubic foot, while the upper curve assumes a mixed phase density of 20 pounds per cubic foot. Knowing the intensity of the source of radiation, the approximate density of the mixed phase, the density of the solidified material, and the wall thickness and material of construction of the container, it is possible to calculate the amount of radiation that would reach a radiation detector. One of the unknowns is the density of the mixed phase. In this case it was assumed that the highest mixed phase density would be 25 pounds per cubic foot, while the lowest mixed phase density would be 20 pounds per cubic foot. Using these parameters the two curves of FIG. 3 were constructed. The alarm set point was tentatively chosen to be about 13.8 indicated by the highest point on the curve for mixed phase density of 25 pounds per cubic foot. This way if the mixed phase density is actually 20 pounds per cubic foot, a chunk of very small thickness will activate the alarm. On the other hand if the mixed phase density should be on the high side that is over 25 pounds per cubic foot, then as shown on the diagram, the thickness of the chunk would have to be 15 centimeters before the alarm would be activated. It was determined that formation of a chunk of material 15 centimeters thick within the container before activation of the alarm would be acceptable in this particular case.

Figure 4:
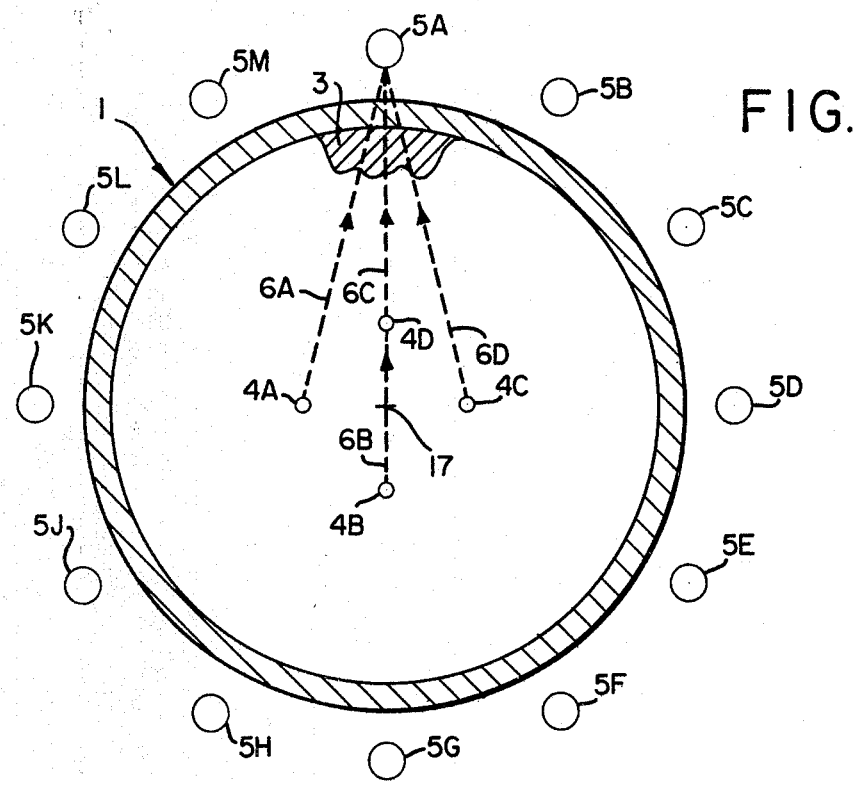
FIG. 4 is a cut away plan view of an embodiment of the invention utilizing more than one radiation source.

If the walls of the container are very thick, the container very large, and/or the mixed phase density very high, then use of more than one radiation source may be necessary. This is illustrated in FIG. 4 where four radiation sources 4A, 4B, 4C and 4D are disposed about center line 17 of container 1. Twelve radiation detectors 5A to 5M are shown disposed about the outside of the container. Radiation from each of the four sources then will reach each radiation detector. For example, radiation reaches detector 5A by flowing along path 6A, 6B, 6D and 6C.

EXAMPLE

Figure 5:
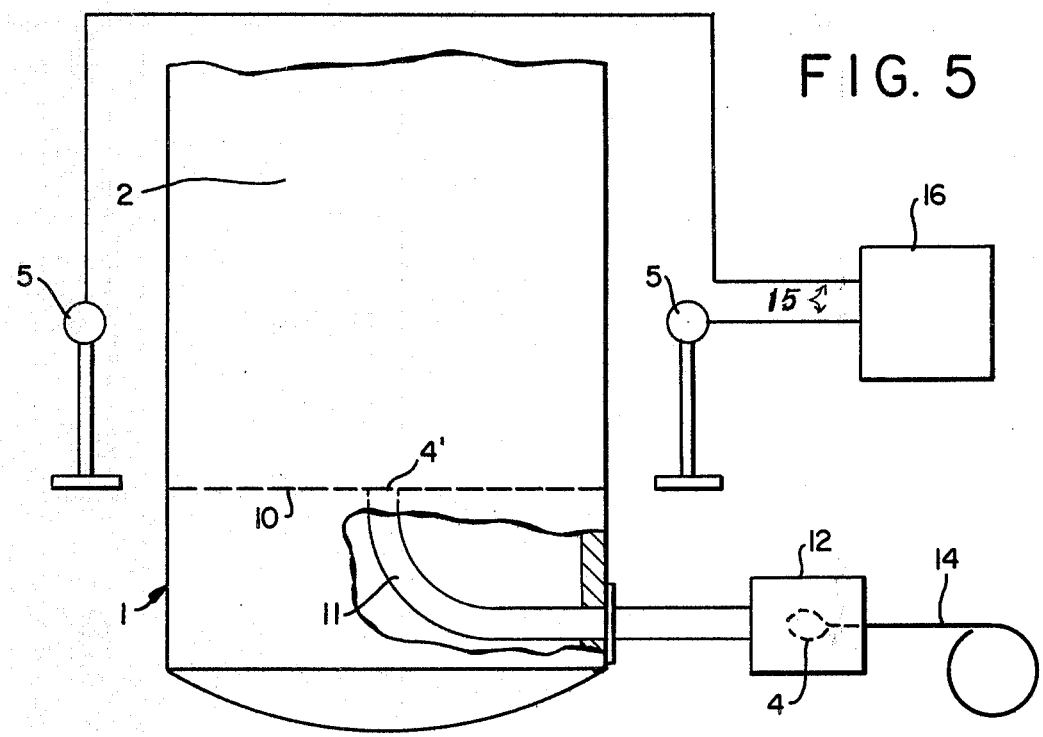
FIG. 5 is an elevational view of a fluidized-bed reactor employing a preferred embodiment of the invention.

Chunk formation occasionally caused difficulty in operating a fluidized bed low pressure olefin polymerization reactor, having a diameter of 8 feet and wall thickness of 0.9375 inches, illustrated in FIG. 5. The chunks would form just above distributor plate 10. It was determined that, if the chunks could be detected and removed before they became large, the difficulty would be eliminated. The density of the solid phase material in chunk form was 60 pounds cubic foot and the fluidized bed density was estimated to be between 20 and 25 pounds per cubic foot. A chunk detection system in accordance with the present invention was installed as described below.

Automatic electronic instrumentation is not necessary to practice this invention but merely preferred. The instrumentation actually used in this example is probably no longer available commercially. However, it is currently possible to purchase instrumentation that is preferred over that actually used. This preferred instrumentation, available from the Ohmart Corporation, 4241 Allendorf Drive, Cincinnati, Ohio 45209; and Panalarm Division of the U.S. Riley Company, 7401 North Hamlin Avenue, Skokie, Ill. 60076, is described below. If desirable, a person having ordinary skill in the art of electronic instrumentation could design alternate instrumentation.

A well for disposing and removing the radiation source consisting of pipe 11 was installed in the reactor. Pipe 11 is three-quarter inch schedule 40 stainless steel pipe bent on a radius of 24 inches to reach the center of the reactor located at 4'. The end of the pipe was closed to form the well. The radiation source used was a 1,000 millicure Cesium 137 source in an Ohmart source holder in accordance with Ohmart drawing C-23166. Eight explosion proof remote radiation detectors illustrated by numeral 5 in FIG. 5 of this specification (similar to those made by Ohmart Corp.) were disposed at equal distance about the perimeter of the reactor just above distributor plate 10. The detectors were wired by wires 15 into a detector control module 16 which was similar to an Ohmart Level Art* 1500 Multi Point Level System module. This in turn was wired into an alarm box indicator (not shown) which was similar to a model 8025 surface mount enclosure with 9 model 82-AM5-24 twin point modules with model 81-F5 flasher and 81-25-120A-5-24 power supply manufactured by the Panalarm Division of the U.S. Riley Company. For safety an area high radiation alarm similar to an Ohmart GM-11R with local audible and visual alarms was installed in the vicinity of the reactor. Flexible cable 14 was used to move the radiation source 4 from radiation source holder 12 into the center of the reactor 4'. Radiation shielding was installed around the radiation source so that the level of radiation in the vicinity of the reactor was low enough to permit unlimited access to the area.
*Trademark or Tradename When the reactor was started up and the radiation source inserted into location 4' by flexible cable 14, the radiation level detected by radiation detectors 5 was higher than expected. This was probably caused by the actual fluid bed density being lower than expected. The radiation source was then shielded to reduce the radiation detected to a more appropriate level. Since the revisions, the unit has been operating successfully detecting the formation and location of chunks within the reactor, thereby preventing the formation of large chunks which, if allowed to grow large, would be very difficult to remove. The present procedure is to shut the reactor down when a small chunk is detected, and to enter the reactor and remove the chunk before it becomes too large for easy removal. The chunks are always located exactly where the instrumentation indicates. The operating personnel have become so satisfied with this invention's performance that they are reluctant to operate this type of reactor unless the chunk detector system is installed and operational.

What is claimed is:

1. A method for detecting solidification in a mixed phase low pressure fluidized bed olefin polymerization reactor having volume comprising:
    A. disposing a radiation source and a radiation detector such that radiation from said radiation source will pass through a radiation path through at least a portion of the volume of said reactor to reach said radiation detector,
    B. detecting solidification in said radiation path by noting a decrease in the amount of radiation reaching said radiation detector.

2. The method of claim 1 comprising disposing said radiation source within said reactor.

3. The method of claim 2 comprising disposing a plurality of radiation detectors at different locations outside said reactor, thereby creating an equal plurality of radiation paths between said radiation source and said radiation detectors.

4. The method of claim 3 comprising using a reactor with a symmetrical shape and disposing said radiation source on a center line of said reactor.

* * * * *